US010485526B2

(12) United States Patent
Haverkost et al.

(10) Patent No.: US 10,485,526 B2
(45) Date of Patent: Nov. 26, 2019

(54) DEVICES AND METHODS FOR REDUCING A DIMENSION OF OPENINGS IN TISSUE

(71) Applicant: Boston Scientific Scimed, Inc., Maple Grove, MN (US)

(72) Inventors: Patrick A. Haverkost, Corcoran, MN (US); Joel N. Groff, Delano, MN (US); Martin R. Willard, Burnsville, MN (US); Anthony Frank Tassoni, Jr., Andover, MN (US); Nicholas Lee Tassoni, Andover, MN (US); Gary John Pederson, Jr., Albertville, MN (US); Joseph Michael Connolly, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 256 days.

(21) Appl. No.: 15/593,977

(22) Filed: May 12, 2017

(65) Prior Publication Data
US 2017/0325821 A1 Nov. 16, 2017

Related U.S. Application Data

(60) Provisional application No. 62/336,827, filed on May 16, 2016.

(51) Int. Cl.
*A61B 17/00* (2006.01)
*A61B 17/128* (2006.01)
(Continued)

(52) U.S. Cl.
CPC ...... *A61B 17/0057* (2013.01); *A61B 17/1227* (2013.01); *A61B 17/1285* (2013.01); *A61F 5/0086* (2013.01); *A61B 17/083* (2013.01); *A61B 2017/00243* (2013.01); *A61B 2017/00575* (2013.01); *A61B 2017/00584* (2013.01); *A61B 2017/00623* (2013.01); *A61B 2017/00867* (2013.01); *A61B 2017/00893* (2013.01); *A61B 2017/00964* (2013.01)

(58) Field of Classification Search
CPC ............ A61B 17/0057; A61B 17/1227; A61B 17/1285; A61B 17/083; A61B 2017/00623; A61B 2017/00584; A61B 2017/00867; A61F 5/0086
See application file for complete search history.

(56) References Cited

U.S. PATENT DOCUMENTS

| 8,361,110 B2 | 1/2013 | Chanduszko | |
| 2003/0093096 A1* | 5/2003 | McGuckin, Jr. ... | A61B 17/0057 606/157 |
| 2003/0225421 A1* | 12/2003 | Peavey ............. | A61B 17/0057 606/151 |

* cited by examiner

*Primary Examiner* — Katherine M Shi
*Assistant Examiner* — Michael G Mendoza
(74) *Attorney, Agent, or Firm* — Bookoff McAndrews, PLLC

(57) ABSTRACT

A clip for reducing a dimension of an opening in tissue may include a continuous member having a plurality of legs and a plurality of preformed bends connecting adjacent legs, wherein the plurality of legs form: a first group having two protrusions; a second group having two protrusions; and a third group having two protrusions, wherein each protrusion of each group includes two legs of the continuous member and a corresponding preformed bend connecting the two legs, and each protrusion of each group extends from a region adjacent a first end of the clip to a region adjacent a second end of the clip.

5 Claims, 4 Drawing Sheets

(51) Int. Cl.
*A61B 17/122* (2006.01)
*A61F 5/00* (2006.01)
*A61B 17/08* (2006.01)

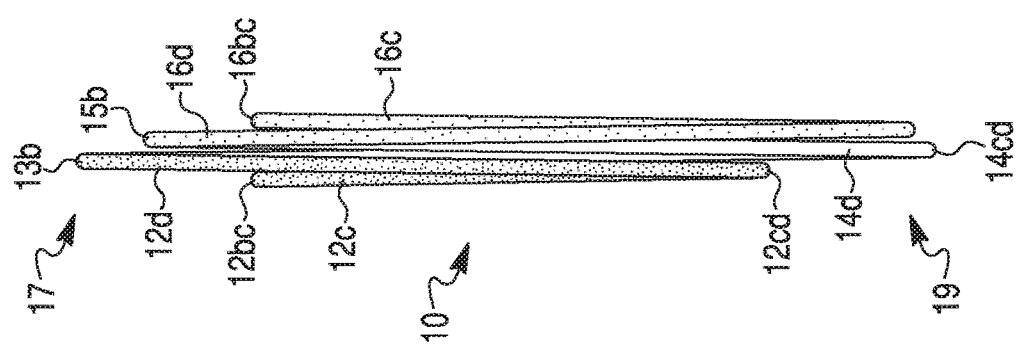
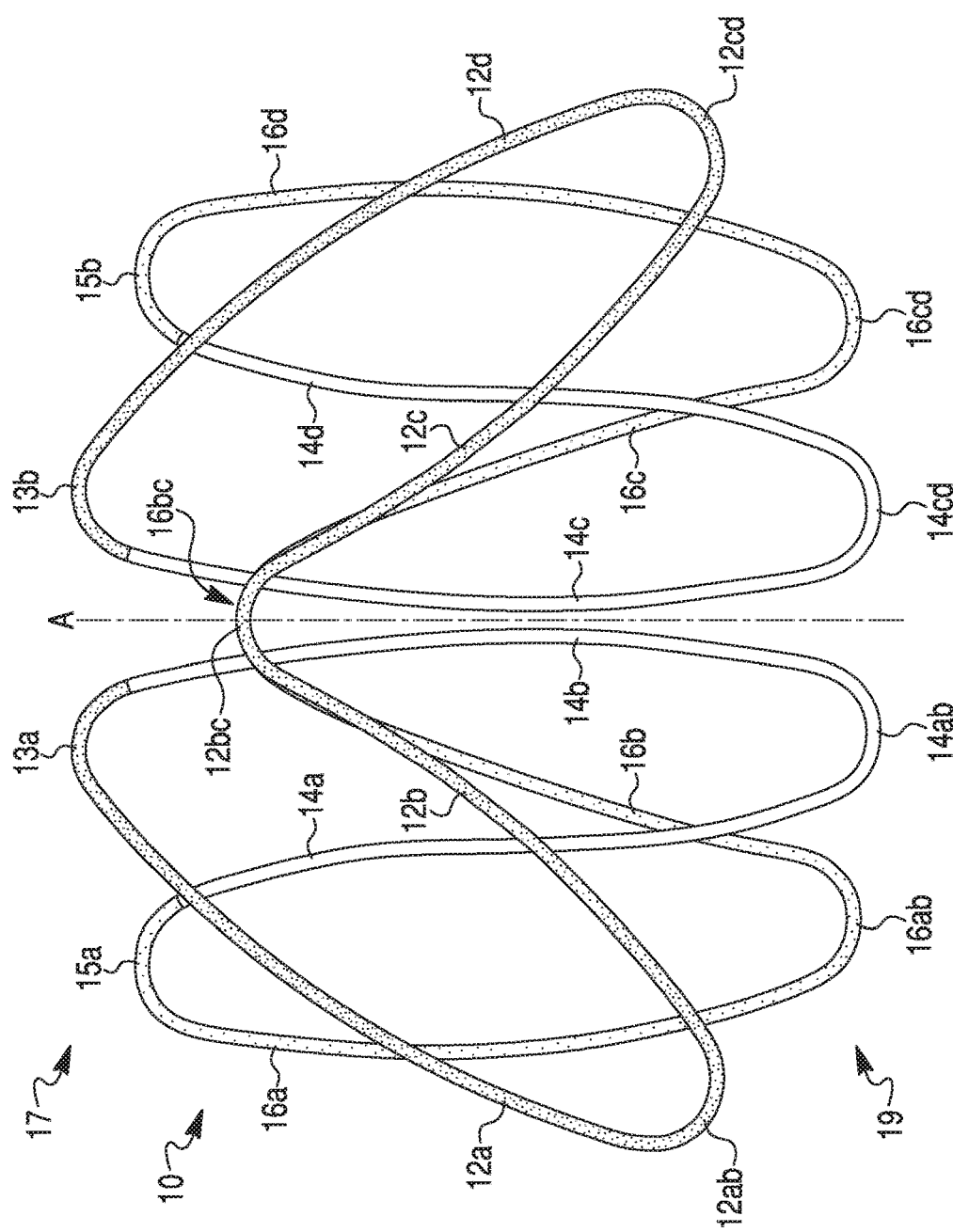

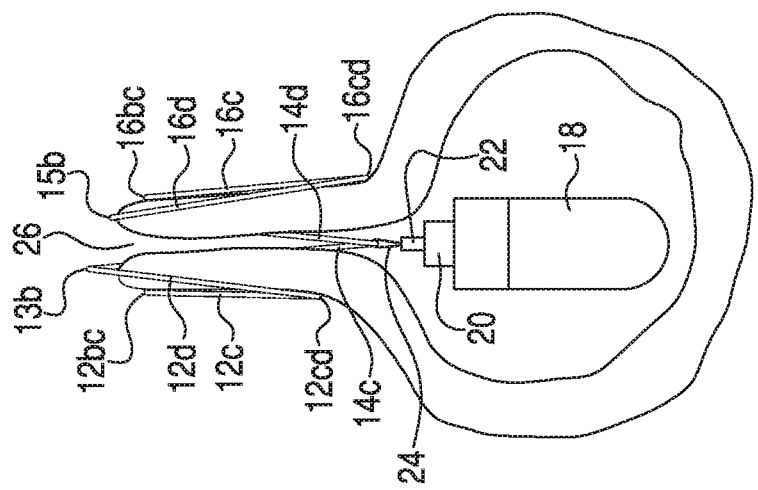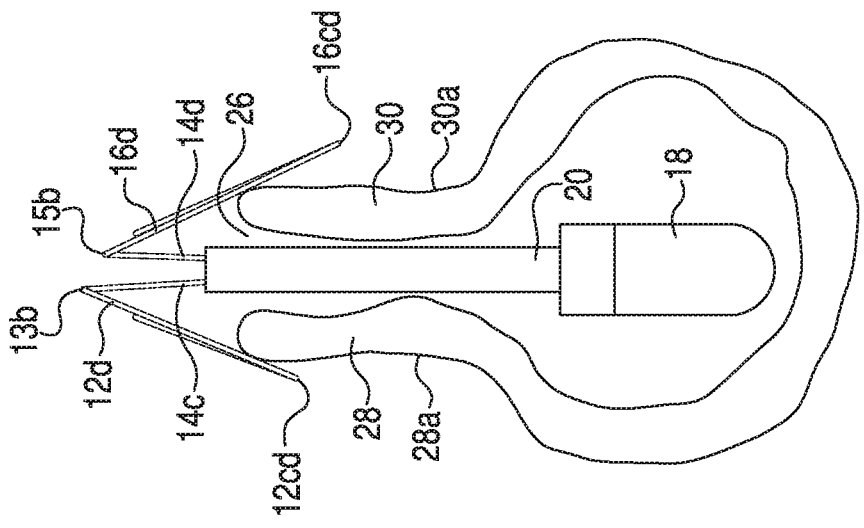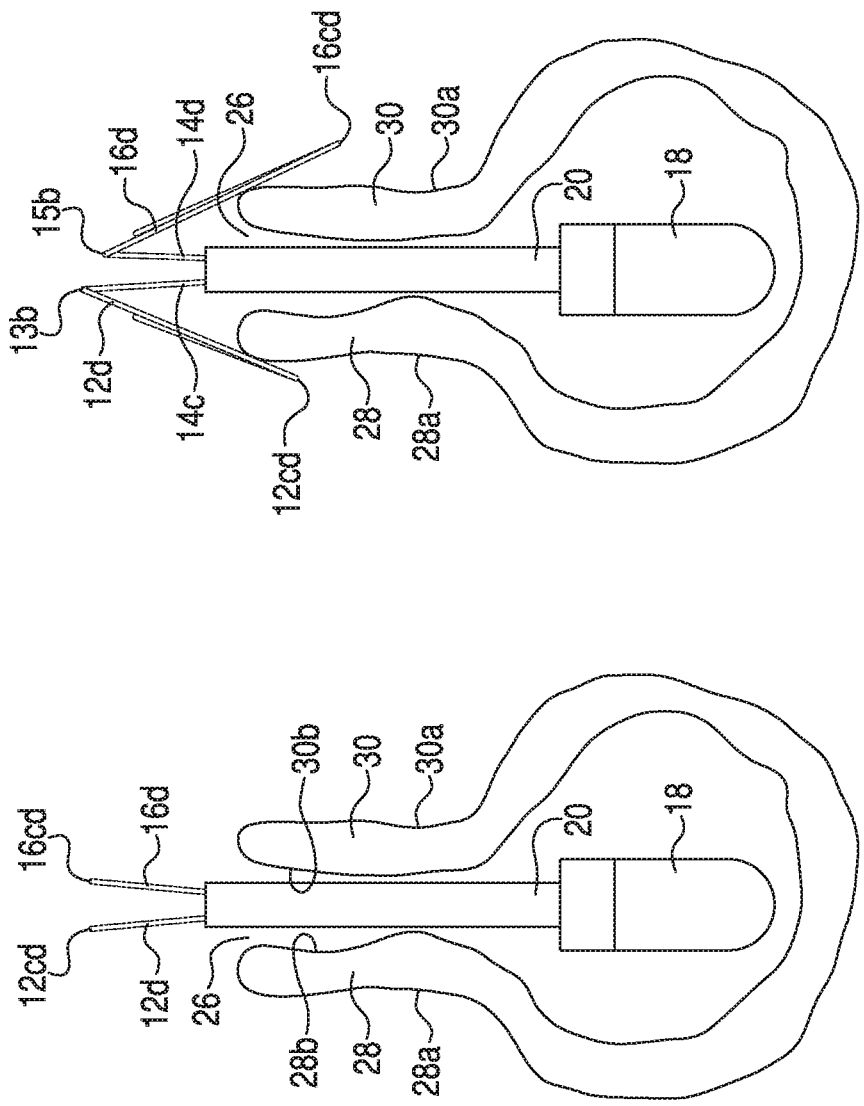

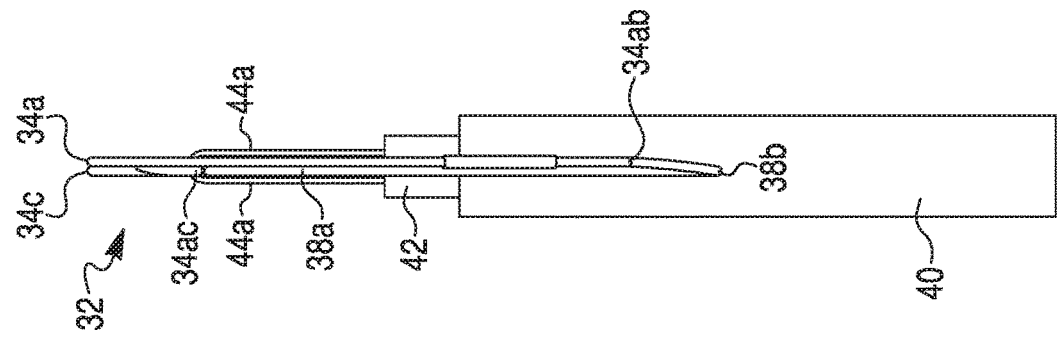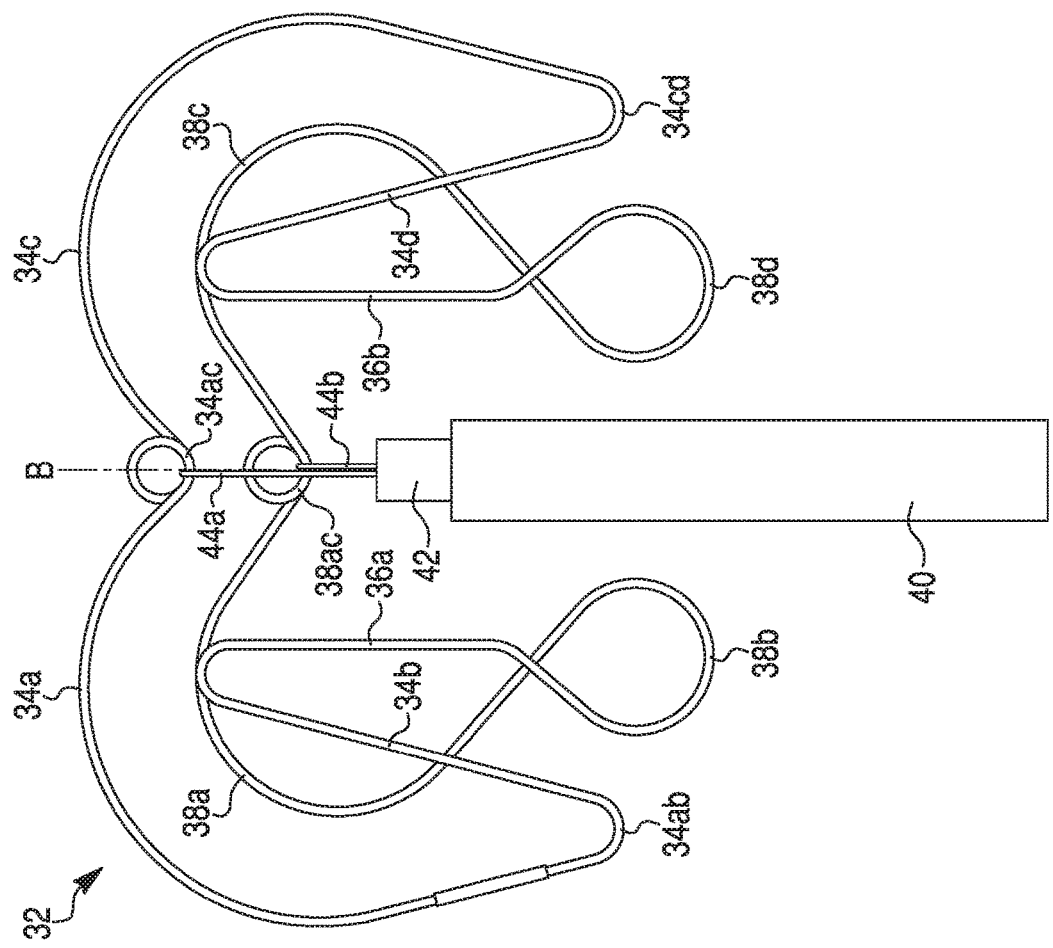

DEVICES AND METHODS FOR REDUCING A DIMENSION OF OPENINGS IN TISSUE

CROSS-REFERENCE TO RELATED APPLICATIONS

This application claims the benefit of priority to U.S. Provisional Application No. 62/336,827, filed on May 16, 2016, which is incorporated by reference herein in its entirety.

TECHNICAL FIELD

This disclosure relates to devices (e.g., clips) and methods for reducing a dimension of openings in tissue. In particular, this disclosure relates to implantable shape memory clips.

BACKGROUND

After undergoing surgical resection (e.g., a sleeve gastrectomy), patients may develop a post-surgical leak. Leaks may complicate recovery and may be more severe for patients who have compromised immune systems. Leaks may cause sepsis or death, and may be costly to treat. Furthermore, some patients cannot withstand the risks of an additional invasive procedure.

SUMMARY

Examples of the present disclosure relate to, among other things, devices (e.g., clips) for reducing a dimension of openings in tissue. Each of the examples disclosed herein may include one or more of the features described in connection with any of the other disclosed examples.

In one example, a clip for reducing a dimension of an opening in tissue may include a continuous member having a plurality of legs and a plurality of preformed bends connecting adjacent legs, wherein the plurality of legs form: a first group having two protrusions; a second group having two protrusions; and a third group having two protrusions, wherein each protrusion of each group includes two legs of the continuous member and a corresponding preformed bend connecting the two legs, and each protrusion of each group extends from a region adjacent a first end of the clip to a region adjacent a second end of the clip.

The clip may additionally or alternatively include one or more of the following features: the clip may be configured to secure a first tissue portion to a second tissue portion, with the first group configured to be positioned adjacent the first tissue portion opposite the second tissue portion, the second group configured to be positioned between the first and second tissue portions, and the third group configured to be positioned adjacent the second tissue portion opposite the first tissue portion; the clip may include a shape memory material; relative to an axis through a center of the clip, the preformed bends corresponding to the first group may be positioned radially outward from the preformed bends corresponding to the third group, and the preformed bends corresponding to the third group may be positioned radially outward from the preformed bends corresponding to the second group; the clip may be configured to transform from a compressed configuration to an expanded configuration; the clip may be configured to be placed in and deployed from a tube such that the first and third groups deploy prior to the second group; and the opening may be in a staple line of a patient.

In another example, a clip for reducing a dimension of an opening in tissue may include a continuous member forming: a first portion configured to be implanted adjacent a first side of a first tissue portion; a second portion configured to be implanted adjacent a second side of the first tissue portion and adjacent a second side of a second tissue portion; and a third portion configured to be implanted adjacent a first side of the second tissue portion, wherein the first portion is connected to the second portion by a first preformed bend and a second preformed bend, wherein the first and second preformed bends are adjacent a first end of the clip, and the third portion is connected to the second portion by a third preformed bend and a fourth preformed bend, wherein the third and fourth preformed bends are adjacent the first end of the clip.

The clip may additionally or alternatively include one or more of the following features: the first portion may include two protrusions, the second portion may include two protrusions, and the third portion may include two protrusions, wherein each protrusion of each portion may include two legs of the member and a corresponding preformed bend connecting the two legs; the corresponding preformed bend of each protrusion may be adjacent a second end of the clip; the clip may include twelve preformed bends and twelve legs, with each leg extending between two preformed bends; the first and second preformed bends may be configured to extend over an edge of the first tissue portion, and the third and fourth preformed bends may be configured to extend over an edge of the second tissue portion; the clip may include a shape memory material; the clip may be configured to be placed in and deployed from a tube such that the first and third portions deploy prior to the second portion; and the opening may be in a staple line of a patient.

In yet another example, a method for deploying a clip may include: inserting a tube into a patient, wherein the tube includes the clip in a compressed configuration, wherein the clip includes a first portion, a second portion, and a third portion; placing at least a portion of the tube between a first tissue portion and a second tissue portion; moving the clip and tube relative to each other to remove the first portion of the clip and the third portion of the clip from the tube; allowing preformed bends of the clip to return to a bent configuration so that at least one preformed bend extends over an edge of the first tissue portion, and the first portion exerts radially inward pressure against an exterior side of the first tissue portion, and at least one preformed bend extends over an edge of the second tissue portion, and the third portion exerts radially inward pressure against an exterior side of the second tissue portion; and moving the clip and tube relative to each other to remove the second portion of the clip from the tube and position the second portion of the clip between the first and second tissue portions.

The method may additionally or alternatively include one or more of the following features or steps: the clip may include a shape memory material; the clip may include a continuous member that forms the first, second, and third portions; the first portion may include at least two protrusions, the second portion may include at least two protrusions, and the third portion may include at least two protrusions, the clip may extend from a first end adjacent the edges of the first and second tissue portions to a second end, and each of the protrusions may extend from a region adjacent the first end of the clip to a region adjacent the second end of the clip; and the first tissue portion may be an anterior wall portion of a stomach, and the second tissue portion may be a posterior wall portion of the stomach.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate examples of the present disclosure and together with the description, serve to explain the principles of the disclosure.

FIG. 1 illustrates a front view of a clip according to a first example.

FIG. 2 illustrates a side view of the clip of FIG. 1.

FIGS. 4A-4C illustrate an exemplary method for implanting the clip of FIG. 1.

FIG. 5 illustrates a front view of a clip according to a second example.

FIG. 6 illustrates a side view of the clip of FIG. 5.

DETAILED DESCRIPTION

Figure 3:
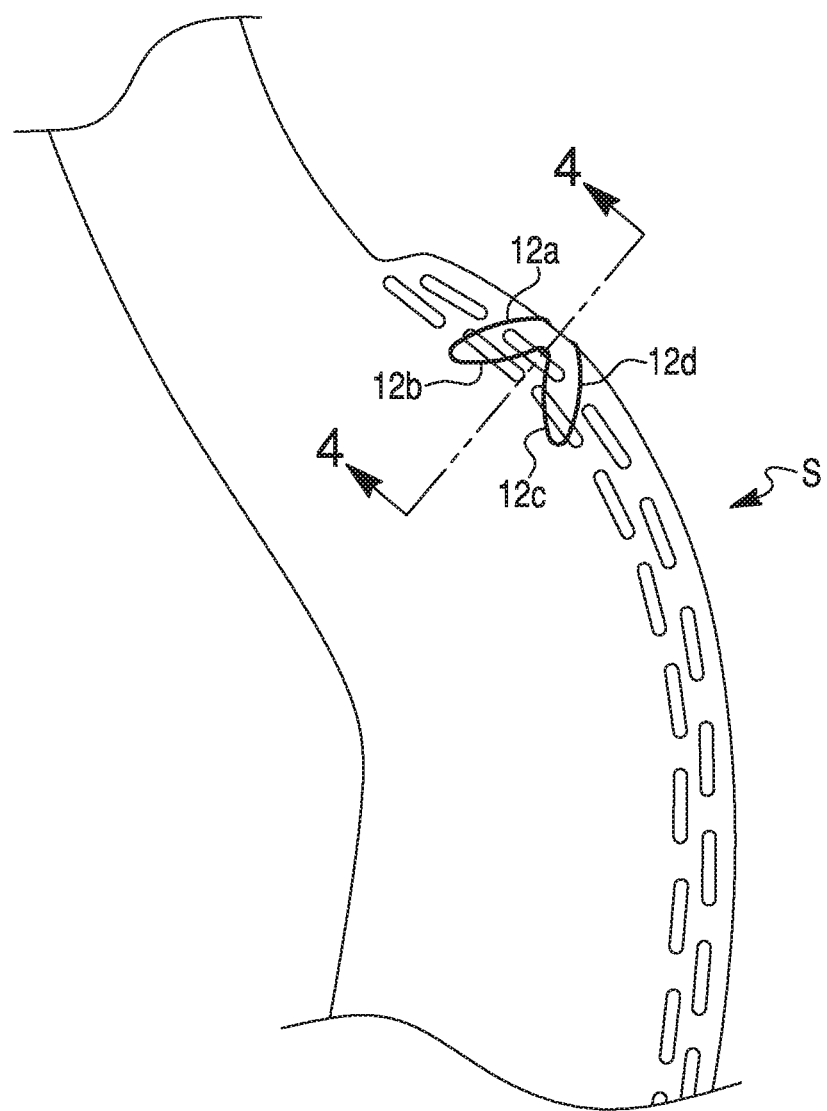
FIG. 3 illustrates the clip of FIG. 1 implanted over an opening in a staple line.

The present disclosure is drawn to devices (e.g., clips) and methods for reducing a dimension of openings in tissue. The opening may be any shape, and the dimension may be, for example, a distance across a region of the opening, a diameter (if the opening is circular), or any other suitable dimension of the opening. The clips described herein may be implanted in a minimally-invasive procedure through the working channel of a catheter, endoscope, or any other elongated device (e.g., delivery device) with a lumen. The clips may include a shape memory material (e.g., Nitinol) to allow them to transform from a collapsed (e.g., elongated) configuration within a delivery device to an expanded configuration within a patient. The clips may be used to repair a leak in a staple line, a patent foramen ovale, or any other opening in tissue.

Referring to FIG. 1, a first example of a clip 10 may include a continuous member with a plurality of preformed bends. The member may be, for example, a wire, cable, or the like. In one example, the angle between the legs on either side of a preformed bend may be 90° or less. In some cases, the legs on either side of a preformed bend may extend substantially parallel to each other (e.g., legs 14a and 16a). Each leg may be substantially straight, although there may be slight curves or other irregularities in the member. In one example, the preformed bends may divide the member into a first group of legs 12a-d (referred to collectively as first group 12), a second group of legs 14a-d (referred to collectively as second group 14), and a third group of legs 16a-d (referred to collectively as third group 16), with each leg extending between two preformed bends. FIGS. 1 and 2 include stippling to better illustrate and describe the various portions of the clip 10. However, the stippling is for purposes of description and does not necessarily represent that the different portions of the clip 10 include different materials, properties, or color, although in one example the different portions may include different materials, properties, or colors.

Referring to the view of FIG. 1, the first group 12 may be positioned closest to the viewer. The second group 14 may be positioned behind the first group 12, and the third group 16 may be positioned behind the second group 14. Referring to the side view of FIG. 2, in general, the first group 12 may be positioned farthest to the left, the second group 14 in the middle (towards the bottom of the figure), and the third group 16 farthest to the right.

Referring to FIG. 1, the legs of the first group 12 may form two protrusions that extend generally outward from a central axis A of the clip 10. The first protrusion may include legs 12a and 12b, and the second protrusion may include legs 12c and 12d. Each protrusion may further extend generally in a direction from a first, proximal end 17 of the clip 10 towards a second, distal end 19 of the clip 10. The bend 12ab connecting the legs 12a and 12b may be the distal end of the first protrusion and may be adjacent the distal end 19 of the clip 10. Similarly, the bend 12cd connecting the legs 12c and 12d may be the distal end of the second protrusion and may be adjacent the distal end 19 of the clip 10. Another preformed bend 12bc may connect the two protrusions of group 12 by connecting leg 12b to leg 12c.

The legs of the second group 14 also may form two protrusions that extend generally downward along axis A of the clip 10 and generally from the proximal end 17 towards the distal end 19. The first protrusion of group 14 may include legs 14a and 14b, and the second protrusion may include legs 14c and 14d. The bend 14ab connecting the legs 14a and 14b may be the distal end of the first protrusion and may be adjacent distal end 19, and the bend 14cd connecting the legs 14c and 14d may be the distal end of the second protrusion and also may be adjacent distal end 19. The bends 14ab and 14cd may be positioned radially inward (e.g., closer to axis A) from the bends 12ab and 12cd. The second group 14 may be connected to the first group 12 by two preformed bends 13a, 13b adjacent proximal end 17 of the clip 10.

Finally, the legs of the third group 16 also may form two protrusions that extend generally outward from axis A and generally from the proximal end 17 towards the distal end 19 of the clip 10. The first protrusion of group 16 may include legs 16a and 16b, and the second protrusion may include legs 16c and 16d. The bend 16ab connecting the legs 16a and 16b may be the distal end of the first protrusion and may be adjacent distal end 19, and the bend 16cd connecting the legs 16c and 16d may be the distal end of the second protrusion and may be adjacent distal end 19. The bends 16ab and 16cd may be positioned radially outward (e.g., farther from axis A) from the bends 14ab and 14cd, but radially inward from the bends 12ab and 12cd. The preformed bend 16bc (behind bend 12bc) may connect the two protrusions of group 16 by connecting leg 16b and leg 16c. The third group 16 may be connected to the second group 14 by two preformed bends 15a, 15b adjacent proximal end 17 of the clip 10.

Referring to the side view of FIG. 2, leg 12d may be visible to the left, and leg 14d may be visible adjacent to the leg 12d (towards the bottom of FIG. 2). Leg 16d may be visible on the other side of leg 14d. Legs 12c and 16c also may be visible in FIG. 2 due to the overlapping wires of the clip 10. In general, in the perspective depicted in FIG. 2, the legs of first group 12 may be positioned towards the left, the legs of second group 14 may be positioned in the center, and the legs of third group 16 may be positioned towards the right.

FIG. 3 illustrates the clip 10 implanted in a patient to repair an opening in a staple line in a stomach S of patient who has undergone a sleeve gastrectomy procedure. In this view, the first group 12 of legs 12a-12d can be seen on a first side of the opening. The second group 14 of legs 14a-14d (not shown) may be positioned within the opening, between the two stapled portions of tissue. The third group 16 of legs 16a-16d (not shown) may be positioned on the opposite side of the opening.

FIGS. 4A-4C illustrate an exemplary method for deploying clip 10 to repair an opening 26 in tissue and place the clip 10 in the position shown in FIG. 3. The cross-sectional views are taken along plane 4-4 of FIG. 3. The clip 10 may be loaded into and deployed from a suitable introducer such as, for example, an endoscope 18. In one example, the clip 10 may be loaded into a tube 20 that is positioned in a working channel of the endoscope 18. The clip 10 may be loaded by flipping the first group 12 and the second group 16 outwards and upwards relative to the second group 14 (e.g., by bringing bends 12ab, 12cd, 16ab, and 16cd from a position at the bottom of FIG. 1 to a position at the top of FIG. 1). Radially inward force then may be applied to all of the legs to bring them towards axis A. In this compressed configuration, the clip 10 may be positioned within a distal portion of tube 20, with the second group 14 in a proximal position and the first group 12 and the third group 16 distal to the second group 14. A pusher 22 (shown in FIG. 4C) may be positioned within the tube 20 proximal to the second group 14.

As each portion of the clip 10 is deployed and relieved from the confines of tube 20, the various legs and bends will resume the preformed configuration of the clip 10 shown in FIG. 1. To deploy the clip 10 from the tube 20, the pusher 22 may be moved distally against the bends 14ab and 14cd. This motion may cause the bends 12ab, 12cd, 16ab, and 16cd to protrude from the distal end of the tube 20 (FIG. 4A). As the user continues to move the pusher 22 distally, the legs of both the first group 12 and the third group 16 may fully emerge from the tube 20, as shown in FIG. 4B. The clip 10 may be biased to its original configuration, shown in FIG. 1. Accordingly, the first group 12 and third group 16 may flip back to their original positions, causing the first group 12 to apply radially inward force against a first tissue portion 28 on a first side of the opening 26 and the third group 16 to apply radially inward force against a second tissue portion 30 on a second side of the opening 26.

The first tissue portion 28 may include a first, exterior side 28a and a second, interior side 28b, and the second tissue portion 30 may include a first, exterior side 30a and a second, interior side 30b. Referring to FIG. 4C, when the first group 12 is in place against a first side 28a of the first tissue portion 28, the preformed bends 13a, 13b may extend around an edge of the first tissue portion 28. Similarly, when the third group 16 is in place against the first side 30a of second tissue portion 30, the preformed bends 15a, 15b may extend around an edge of the second tissue portion 30. The tube 20 may then be retracted proximally to expose the second group 14 from the tube 20, now positioned within the opening 26 between the first and second tissue portions 28, 30, as shown in FIG. 4C. One or more tethers 24 may connect bends 14ab and 14cd to the distal end of the pusher 22, such that a user may pull the pusher 22 proximally to adjust the positioning of the clip 10. In an alternative example, the bends 14ab and 14cd may include loops or openings to provide an attachment point for the tether 24. Once implanted, the one or more tethers 24 may be removed from clip 10.

The clip 10 may be used to treat openings in which two tissue portions lie adjacent to an opening. In one example, as shown in FIGS. 4A-4C, the two tissue portions may lie substantially parallel to each other. However, the clip 10 may additionally or alternatively be used to close an opening in which the two tissue portions initially lie in substantially the same plane (e.g., tissue around an opening in a wall of an organ). In this example, the clip 10 may be deployed in the same manner through the opening in tissue, and the radially inward force of the first group 12 and the third group 16 may pull the sides of the opening together such that they are pulled into a substantially parallel configuration and secured by the clip in a similar manner as shown in FIG. 4C.

FIG. 5 illustrates a front view of an alternative embodiment of a clip 32 and FIG. 6 illustrates a left side view of clip 32. The clip 32 may be used to treat a patent foramen ovale or any other suitable opening in tissue. In one example, the clip 32 may be formed of a continuous member, similar to clip 10, and the member may include a shape memory material. A first group of lengths 34a, 34b, 34c, and 34d (referred to collectively as first group 34) may be positioned in a first cavity of an organ (e.g., in the left atrium of the heart), a second group of lengths 36a and 36b (referred to collectively as second group 36) may be positioned to extend from the first cavity to a second cavity (e.g., between two tissue portions), and a third group of lengths 38a, 38b, 38c, and 38d (referred to collectively as third group 38) may be positioned in a second cavity of an organ (e.g., in the right atrium of the heart).

Referring to first group 34, lengths 34a and 34c, beginning proximate axis B and in the orientation of FIG. 5, may each curve slightly upward and radially outward. Each length 34a, 34c may then curve downward, first in a radially outward direction and then in a radially inward direction, towards bends 34ab and 34cd, respectively, such that together, the lengths 34a and 34c form an "M" shape. A loop may be formed at bend 34ac between lengths 34a and 34c for attachment of a tether 44a. Lengths 34b and 34d may each extend from bends 34ab and 34cd, respectively, upwards and slightly radially inwards towards axis B.

Referring to second group 36, lengths 36a and 36b may connect lengths 34b and 34d, respectively, of first group 34, to loops 38b and 38d, respectively, of third group 38. Each of lengths 36a and 36b may extend substantially parallel to axis B.

With respect to third group 38, lengths 38a and 38c may form curves similar in shape to the lengths 34a and 34c of group 34. However, the lengths 38a and 38c may have regions with a higher curvature than lengths 34a and 34c and therefore may extend radially inward to a greater degree back towards axis B. A loop may be formed at bend 38ac between lengths 38a and 38c for attachment of a tether 44b. Lengths 38b and 38d may form loops that connect the lengths 36a, 36b of the second group 36 to lengths 38a, 38c, respectively, of the third group 38.

The clip 32 may be positioned in a compressed (e.g., elongated) configuration for loading into a tube. To transform the clip 32 to the compressed configuration, first group 34 may be flipped outwards and upwards. In other words, the bends 34ab and 34cd may be brought from a position at the bottom of FIG. 5 to a position at the top of FIG. 5. Then, the third group 38 may be flipped downwards and stretched, such that the bend 38ac is at a proximal-most position, and loops 38b and 38d are stretched out such that the portion of the member forming those loops is substantially straight. Radially inward force may then be applied to all of the lengths of clip 32 to bring them towards axis B. In this configuration, the clip 30 may be positioned within a distal portion of tube 40, with the bend 38ac at a proximal end and the bends 34ab and 34cd at a distal end.

As each portion of the clip 32 is deployed and relieved from the confines of tube 40, the various lengths will resume the preformed configuration shown in FIG. 5. To deploy the clip 32 from the tube 40, a pusher 42 may be moved distally against the bend 38ac. This motion may cause the bends 34ab and 34cd to protrude from the distal end of the tube 40, followed by lengths 34b, 34d and 34a, 34c. When lengths 34a and 34c are about halfway complete with their exit from tube 40, lengths 36a and 36b begin exiting the tube 40. The user may adjust the position of the tube 40 to ensure that the lengths 36a and 36b are positioned between the two overlapping tissue portions of the patent foramen ovale. Following lengths 36a and 36b, the portion of the member forming loops 38b and 38d may begin exiting the tube 40, followed by the portion of the member forming lengths 38a and 38c. Finally, bend 38ac may be pushed out of the tube 40. Tether 44a may connect to the loop at bend 34ac and tether 44b may connect to the loop at bend 38ac. Once the clip 32 has been deployed from the tube 40, the tethers 44a, 44b may be used to pull the clip 32 and adjust its position.

In additional or alternative examples, the clips described herein may include protrusions, such as texturing or spikes, to facilitate gripping of tissue. The protrusions in some examples may damage the tissue to stimulate tissue growth around the clip, which may be useful to maintain the implanted position of the clip. The clips may include a drug-delivery coating. In some examples, the clips may include regions that provide stress relief (e.g., at the preformed bends). The stress relief regions may include a material of a different flexibility or strength to increase the ability of the stress relief regions to withstand motions of the tissue. In one example, the member may include a zigzag shape in a stress relief region. The zigzag configuration may allow the stress relief region to lengthen and shorten in connection with tissue movements.

While principles of the present disclosure are described herein with reference to illustrative examples for particular applications, it should be understood that the disclosure is not limited thereto. Those having ordinary skill in the art and access to the teachings provided herein will recognize additional modifications, applications, examples, and substitution of equivalents all fall within the scope of the embodiments described herein. Accordingly, the invention is not to be considered as limited by the foregoing description.

We claim:

1. A method for deploying a clip, comprising:
    inserting a tube into a patient, wherein the tube includes the clip in a compressed configuration, wherein the clip includes a first portion, a second portion, and a third portion;
    placing at least a portion of the tube between a first tissue portion and a second tissue portion;
    moving the clip and tube relative to each other to remove the first portion of the clip and the third portion of the clip from the tube;
    allowing preformed bends of the clip to return to a bent configuration so that at least one preformed bend extends over an edge of the first tissue portion, and the first portion exerts radially inward pressure against an exterior side of the first tissue portion, and at least one preformed bend extends over an edge of the second tissue portion, and the third portion exerts radially inward pressure against an exterior side of the second tissue portion; and
    moving the clip and tube relative to each other to remove the second portion of the clip from the tube and position the second portion of the clip between the first and second tissue portions.

2. The method of claim 1, wherein the clip includes a shape memory material.

3. The method of claim 1, wherein the clip includes a continuous member that forms the first, second, and third portions.

4. The method of claim 1, wherein the first portion includes at least two protrusions, the second portion includes at least two protrusions, and the third portion includes at least two protrusions, the clip extends from a first end adjacent the edges of the first and second tissue portions to a second end, and each of the protrusions extends from a region adjacent the first end of the clip to a region adjacent the second end of the clip.

5. The method of claim 1, wherein the first tissue portion is an anterior wall portion of a stomach, and the second tissue portion is a posterior wall portion of the stomach.

\* \* \* \* \*